United States Patent
Gebre

(10) Patent No.: US 11,490,877 B2
(45) Date of Patent: Nov. 8, 2022

(54) SYSTEM AND METHOD OF IDENTIFYING CHARACTERISTICS OF ULTRASOUND IMAGES

(71) Applicant: KONINKLIJKE PHILIPS N.V., Eindhoven (NL)

(72) Inventor: Binyam Gebrekidan Gebre, Rosmalen (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 142 days.

(21) Appl. No.: 16/977,889

(22) PCT Filed: Mar. 4, 2019

(86) PCT No.: PCT/EP2019/055256
§ 371 (c)(1),
(2) Date: Sep. 3, 2020

(87) PCT Pub. No.: WO2019/170573
PCT Pub. Date: Sep. 12, 2019

(65) Prior Publication Data
US 2021/0068791 A1    Mar. 11, 2021

(30) Foreign Application Priority Data
Mar. 8, 2018  (EP) .................................. 18160635

(51) Int. Cl.
*A61B 8/08*   (2006.01)
*A61B 8/00*   (2006.01)
*G06T 7/11*   (2017.01)

(52) U.S. Cl.
CPC .......... *A61B 8/5207* (2013.01); *A61B 8/4254* (2013.01); *A61B 8/488* (2013.01);
(Continued)

(58) Field of Classification Search
CPC ..... A61B 8/4254; A61B 8/488; A61B 8/5207; A61B 8/5223; A61B 8/5292;
(Continued)

(56) References Cited

U.S. PATENT DOCUMENTS

| 11,064,977 B2* | 7/2021 | McLaughlin | .......... G06V 10/82 |
| 2015/0256761 A1* | 9/2015 | Umezawa | ............ A61B 8/5207 348/77 |

(Continued)

FOREIGN PATENT DOCUMENTS

WO    2017151757 A1    9/2017

OTHER PUBLICATIONS

International Search Report and Written Opinion for International Application No. PCT/EP2019/055256, filed Mar. 4, 2019, 14 pages.
(Continued)

*Primary Examiner* — Bobbak Safaipour

(57) ABSTRACT

The invention provides a method for identifying a characteristic of one or more ultrasound images, wherein each image is of a subject imaged by an ultrasound probe using an ultrasound imaging process. The method includes obtaining a manipulation signal indicative of a manipulation of the ultrasound probe during the imaging process. A portion of the manipulation signal, which indicates the manipulation of the probe during a time period, is obtained. The obtained portion is associated with one or more ultrasound images. A neural network system is then used to classify a characteristic of the one or more ultrasound images based on both the obtained portion of the manipulation signal and the one or more images themselves. Such classification comprises applying one or more convolution kernels on the obtained portion of the manipulation signal to generate a convolution output representative of the obtained portion of the manipulation signal, and classifying the convolution output to
(Continued)

indicate the characteristic of the one or more ultrasound images associated with the obtained portion.

15 Claims, 4 Drawing Sheets

(52) U.S. Cl.
CPC ...... *G06T 7/11* (2017.01); *G06T 2207/10132* (2013.01); *G06T 2207/20081* (2013.01); *G06T 2207/20084* (2013.01); *G06T 2207/30004* (2013.01); *G06T 2207/30168* (2013.01)

(58) Field of Classification Search
CPC ................ G06K 9/6218; G06K 9/6247; G06T 2207/10132; G06T 2207/20081; G06T 2207/20084; G06T 2207/30004; G06T 2207/30168; G06T 7/00; G06T 7/11; G16H 50/20; G16H 50/30; G06V 10/82; G06V 2201/031
See application file for complete search history.

(56) References Cited

U.S. PATENT DOCUMENTS

| | | | |
|---|---|---|---|
| 2016/0048737 A1* | 2/2016 | Kam | G06T 7/0012 382/131 |
| 2016/0155227 A1 | 6/2016 | Chae | |
| 2017/0143312 A1 | 5/2017 | Hedlund et al. | |
| 2018/0055483 A1* | 3/2018 | Hunter | A61B 8/467 |
| 2020/0214676 A1* | 7/2020 | McLaughlin | G06T 5/001 |
| 2020/0229797 A1* | 7/2020 | Yu | G01S 7/52026 |
| 2021/0177373 A1* | 6/2021 | Xie | G06N 3/04 |
| 2021/0267570 A1* | 9/2021 | Ulman | A61B 8/5223 |
| 2021/0350529 A1* | 11/2021 | Ayinde | G06T 7/0012 |

OTHER PUBLICATIONS

Chen, et al., "Iterative Multi-domain Regularized Deep Learning for Anatomical Structure Detection and Segmentation from Ultrasound Images", MICCAI 2016, Part II, LNCS 9901, pp. 487 495.

Yang, et al., "Fine-Grained Recurrent Neural Networks for Automatic Prostate Segmentation in Ultrasound Images", Proceedings of the Thirty-First AAAI Conference on Artificial Intelligence (AAAI-17), pp. 1633-1639, Feb. 12, 2017.

Ronneberger, et al., "U-Net: Convolutional Networks for Biomedical Image Segmentation", Cornell University, Dept. of Computer Science, Faculty of Engineering, Computer Vision and Pattern Recognition, submitted on May 18, 2015, pp. 1-8.

Bahner, et al. "Language of Transducer Manipulation." Journal of Ultrasound in Medicine 35.1 (2016): 183-188.

Ihnatsenka, et al. "Ultrasound: Basic understanding and learning the language" International journal of shoulder surgery, 4(3), 55, Jul. 2010.

* cited by examiner

SYSTEM AND METHOD OF IDENTIFYING CHARACTERISTICS OF ULTRASOUND IMAGES

RELATED APPLICATION

This application is the U.S. National Phase application under 35 U.S.C. § 371 of International Application No. PCT/EP2019/055256, filed on Mar. 4, 2019, which claims the benefit and priority of European Application No. 18160635.1, filed Mar. 8, 2018. These applications are hereby incorporated by reference herein.

FIELD OF THE INVENTION

This invention relates to the field of ultrasound image processing and, in particular, to the field of automatic feature characterization within an ultrasound image.

BACKGROUND OF THE INVENTION

Ultrasound imaging is increasingly being employed in a variety of different applications. It is important to provide a user with sufficient information about the subject being scanned, in order to accurately assess a condition of a subject. This is especially the case when the subject in question is a patient undergoing a medical ultrasound scan. Some ultrasound imaging systems comprise an ultrasound probe for obtaining one or more ultrasound images of the subject. Ultrasound probes are usually adapted to be held by a user or clinician of the ultrasound imaging system.

Ultrasound probes may comprise a CMUT transducer array for transmitting ultrasound waves and receiving echo information. The received echo information is processed to generate one or more ultrasound images. The transducer array may alternatively comprise piezoelectric transducers formed of materials such as PZT or PVDF. The transducer array may comprise a two-dimensional array of transducers capable of scanning in a 2D plane or in three dimensions for 3D imaging. In another example, the transducer array may be a 1D array.

There has been an increasing desire to identify characteristics of ultrasound images. These characteristics may include, amongst others, features present in the ultrasound image or a quality of the ultrasound image. A high-quality ultrasound image is required to allow for accurate detection of anomalies or accurate measurement of features in the ultrasound image. Typically, characteristics of an ultrasound image are detected by performing an image processing methodology on a captured ultrasound image.

US 2016/048737 A1 describes an apparatus for adaptive computer-aided diagnosis (CAD) of ultrasound medical images, which includes an image analysis algorithm selector configured to select an image analysis algorithm based on a speed of a probe or a resolution of a current image frame obtained by the probe, and an image analyzer configured to detect and classify a region of interest (ROI) in the current image frame using the selected image analysis algorithm.

US 2016/155227 A1 also relates to a CAD apparatus based on the determination of the diagnostic intention of a user. The CAD apparatus includes a ROI detector configured to detect a ROI from an image input from a probe, and a probe motion determiner configured to determine a motion of the probe in response to the ROI detector detecting the ROI. The CAD apparatus further includes a diagnostic intention determiner configured to determine a diagnostic intention of a user based on the determined motion of the probe, and a diagnostic intention processor configured to perform a diagnostic procedure based on the determined diagnostic intention of the user.

SUMMARY OF THE INVENTION

The invention is defined by the claims.

According to examples in accordance with an aspect of the invention, there is provided a computer-implemented method of identifying a characteristic of one or more ultrasound images, wherein each ultrasound image is of a subject imaged by an ultrasound probe using an ultrasound imaging process, the method comprising:

obtaining a manipulation signal indicative of a manipulation of the ultrasound probe during the ultrasound imaging process;

obtaining a portion of the manipulation signal, the obtained portion indicating the manipulation of the ultrasound probe during a time period, wherein the obtained portion is associated with one or more ultrasound images; and classifying, using a neural network system, a characteristic of the one or more associated ultrasound images based on both the one or more ultrasound images and the obtained portion of the manipulation signal. The step of classifying the characteristic of the one or more associated ultrasound images comprises applying one or more convolution kernels on the obtained portion of the manipulation signal to generate a convolution output representative of the obtained portion of the manipulation signal, and classifying the convolution output to indicate the characteristic of the one or more ultrasound images associated with the obtained portion.

Thus, there is proposed a method of identifying characteristics of an ultrasound image by analyzing or classifying both the ultrasound image and a manipulation signal of the ultrasound probe capturing said ultrasound image. A portion of a manipulation signal is associated with one or more ultrasound images, the portion representing the manipulation (e.g., the spatial movement) of the ultrasound probe during a time period associated with the capture of at least one ultrasound image. The portion of the manipulation signal is classified to help identify a characteristic of the associated ultrasound image(s). In this way, a manipulation signal can be processed to aid in identifying characteristics of the ultrasound image.

The present invention proposes that the way in which an ultrasound probe is manipulated affects or indicates a characteristic of an ultrasound image. Thus, characteristics of a manipulation signal (indicative of the manipulation of an ultrasound probe) may help to define characteristics of ultrasound images collected by the ultrasound probe. Information about an ultrasound image may be identified by processing or analyzing a manipulation signal. In particular, the convolution kernels may capture a convolution output representative, such as a local temporal pattern, of an obtained portion, which may then be advantageously used in identifying a characteristic of the one or more ultrasound images associated with said obtained portion. By classifying an extract of the manipulation signal, and especially the convolution outputs thereof, in conjunction with the associated ultrasound image, a characteristic of one or more ultrasound image associated with that extract can be identified.

That is, in accordance with the present invention, the neural network system takes as inputs both the one or more ultrasound images and the obtained portion of the manipulation signal, and processes them to classify a characteristic of the one or more associated ultrasound images. The processing performed by the neural network system includes generating convolution outputs representative of the obtained portion of the manipulation signal, which will be subsequently used in the neural network system together with the one or more ultrasound images and/or portions thereof, and possibly also with outputs representative of the one or more ultrasound images and/or portions thereof generated by intermediate processing stages of the neural network system, to classify the characteristic of the one or more associated ultrasound images.

In a preferred embodiment, the step of classifying the characteristic of the one or more associated ultrasound images comprises:

using a first neural network comprised in the neural network system to generate the convolution output representative of the obtained portion of the manipulation signal and to classify said convolution output to indicate a manipulation pattern of the ultrasound probe; and classifying, using a second neural network comprised in the neural network system, the characteristic of the one or more associated ultrasound images based on the one or more ultrasound images and the manipulation pattern.

By way of example, it may be known that different features (e.g. regions of interest, such as organs) of a subject are captured when different movements of the ultrasound probe are made. By classifying the portion of a manipulation signal, being a time extract of the manipulation signal, associated with an ultrasound image as being similar to or identical to a particular movement, detection of the features of a subject may be improved.

The proposed invention thereby allows characteristics of an ultrasound image to be identified wherein, using the manipulation signal in conjunction with the ultrasound image may provide additional or more accurate information to that found in the ultrasound image alone. Proposed concepts thereby allow for automated and more accurate characterization of an ultrasound image.

In an embodiment, the step of classifying the characteristic of the one or more associated ultrasound images comprises:

a) classifying whether the obtained portion of the manipulation signal is associated with one of:
  a high-quality ultrasound image;
  an ultrasound image of a predetermined view of the subject; and
  a presence of one or more predetermined regions of interest of the subject in the associated one or more ultrasound images; and
b) identifying the characteristic of the one or more associated ultrasound images by means of assigning the classification of the obtained portion as the characteristic of the one or more associated ultrasound images. That is, the identification of the characteristic of the one or more associated ultrasound images comprises assigning the classification of the obtained portion as the characteristic of the one or more associated ultrasound images.

As previously explained, a manipulation signal may help define or indicate characteristics of ultrasound images captured during generation of that manipulation signal. The above characteristics (quality of the ultrasound image, viewpoint of the ultrasound image and presence of particular features of the subject in an ultrasound image) have been found to be particularly identifiable in a manipulation signal.

The method may therefore identify from the ultrasound images and the manipulation signal whether an ultrasound image depicts a desired area or region of interest, or is of a reasonable quality.

Identifying whether or not predetermined regions of interest are found in the one or more ultrasound images or whether the ultrasound image is of a predetermined view allows for improved labelling, annotating or segmentation of the image. Some ultrasound guidance standards require particular views of a subject (e.g. a fetus) to be obtained for the purposes of screening or analysis. Automated detection of a view of the subject allows such standards to be met with greater precision and ease.

Identifying whether or not an ultrasound image is of a high quality allows for automated disposal of low-quality images (which are typically not useful for analysis of a subject), thereby reducing a memory storage requirement and reducing a burden on a user of an ultrasound system.

In a further embodiment, the step of classifying the characteristic of the one or more associated ultrasound images comprises:

segmenting the manipulation signal into a plurality of portions, each portion being associated with a same one or more ultrasound images;

applying one or more convolutional kernels to each obtained portion of the manipulation signal to generate a convoluted output of each time segment; and processing the convoluted output of each time segment using a long short-term memory to classify each obtained portion.

The convolution kernels may capture a convolution output representative, such as a local temporal pattern, of an obtained portion. Each local temporal pattern may then be processed to build up a long term temporal pattern of the movement of the probe during the image acquisition time window. This may be done, for example, by way of a long short-term memory architecture.

In an embodiment:
the step of obtaining a manipulation signal comprises obtaining a plurality of manipulation signals, each indicative of a manipulation of the ultrasound probe during the ultrasound imaging process;

the step of obtaining a portion of the manipulation signal comprises obtaining a plurality of temporally associated portions by obtaining a temporally associated portion from each manipulation signal, wherein the plurality of temporally associated portions are associated with a same one or more ultrasound images; and the step of classifying the characteristic of the one or more associated ultrasound images comprises classifying the plurality of temporally associated portions to indicate a characteristic of the one or more associated ultrasound images.

In a further embodiment, the step of classifying the plurality of temporally associated portions comprises:

obtaining a two-dimensional data structure representative of the plurality of temporally associated portions;

applying a convolutional kernel to the two-dimensional data structure to generate a convolution output of the two-dimensional data structure; and classifying the convolutional output to indicate a characteristic of the one or more associated ultrasound images.

By applying a convolution kernel to the two dimensional data structure of the obtained portion of the manipulation signal, it is possible to process the manipulation signal using a convolutional neural network. In this way, the local temporal patterns in the manipulation signals may be identified and used in conjunction with the ultrasound images to classify a characteristic of said ultrasound images.

In a yet further embodiment:

the step of obtaining a portion of the manipulation signal comprises obtaining two or more pluralities of temporally associated portions of the manipulation signals, wherein each of the pluralities are associated with a same one or more ultrasound images; and the step of classifying the characteristic of the one or more associated ultrasound images comprises:

a) obtaining a plurality of two-dimensional data structures, each data structure being representative of a different plurality of temporally associated portions;

b) applying a convolutional kernel to each two-dimensional data structure to generate a respective plurality of convolution outputs; and c) processing the plurality of convolution outputs using a long short-term memory to classify the two or more pluralities of temporally associated portions and thereby indicate a characteristic of the one or more associated ultrasound images.

In this way, it is possible to obtain both the local temporal patterns form the convolution neural network and patterns over a longer temporal span using the long short-term memory. By taking both patterns into account, a more accurate description of the manipulation of the probe may be established, thereby increasing the accuracy of the characteristic classification.

In an arrangement, the manipulation is indicative of one or more of:

a location of the ultrasound probe with respect to the subject;

an angle of the ultrasound probe with respect to the subject;

an orientation of the ultrasound probe with respect to the subject;

a pressure applied by the ultrasound probe on the subject;

an acceleration of the ultrasound probe with respect to the subject;

a direction of movement of the ultrasound probe; and a pattern of movement of the ultrasound probe.

By taking one or more of these factors into account, it is possible to gain a more accurate profile of the motion of the ultrasonic probe when collecting the one or more ultrasound images, thereby increasing the accuracy of the characteristic identification.

In some embodiments, the computer-implemented method described above may further comprise segmenting the ultrasound image.

In this way, it is possible to identify features, such as organs or skeletal structures, within the ultrasound image based on the classifications of the manipulation signals and the one or more ultrasound images collected by the probe.

In a further embodiment, the computer-implemented method described above may further comprise overlaying, on each selected ultrasound image, a respective segmented region of interest.

In this way, the identified region of interest may be enhanced on the ultrasound images, thereby allowing a user of the ultrasound system to more easily view and investigate a said region.

According to examples in accordance with an aspect of the invention, there is provided a computer program comprising code means for implementing the computer-implemented method as described above when said program is run on a computer.

According to examples in accordance with an aspect of the invention, there is provided an ultrasound image processing system adapted to identify a characteristic of an ultrasound image, wherein the ultrasound image is of a subject imaged by an ultrasound probe using an ultrasound imaging process, the ultrasound image processing system being adapted to:

obtain a manipulation signal indicative of a manipulation (e.g., a spatial movement) of the ultrasound probe during the ultrasound imaging process;

obtain a portion of the manipulation signal, the obtained portion indicating a manipulation of the ultrasound probe during a time period, wherein the obtained portion is associated with one or more ultrasound images; and classify, using a neural network system, a characteristic of the one or more associated ultrasound images based on both the one or more ultrasound images and the obtained portion of the manipulation signal.

In particular, the ultrasound image processing system is adapted to classify the characteristic of the one or more associated ultrasound images by:

applying one or more convolution kernels on the obtained portion of the manipulation signal to generate a convolution output representative of the obtained portion of the manipulation signal; and classifying the convolution output to indicate the characteristic of the one or more ultrasound images associated with the obtained portion.

In a further embodiment, the ultrasound image processing system is adapted to classify the characteristic of the one or more associated ultrasound images by:

segmenting the manipulation signal into a plurality of portions, each portion being associated with a same one or more ultrasound images;

applying one or more convolutional kernels to each obtained portion of the manipulation signal to generate a convoluted output of each time segment; and processing the convoluted output of each time segment using a long short-term memory to classify each obtained portion.

In another embodiment, the ultrasound image processing system is adapted to:

obtain a plurality of manipulation signals, each indicative of a manipulation of the ultrasound probe during the ultrasound imaging process;

obtain a plurality of temporally associated portions by obtaining a temporally associated portion from each manipulation signal, wherein the plurality of temporally associated portions are associated with a same one or more ultrasound images; and classify the plurality of temporally associated portions to indicate a characteristic of the one or more associated ultrasound images.

Preferably, the ultrasound image processing system is adapted to classify the plurality of temporally associated portions by:

obtaining a two-dimensional data structure representative of the plurality of temporally associated portions;

applying a convolutional kernel (310) to the two-dimensional data structure to generate a convolution output of the two-dimensional data structure; and classifying the convolutional output to indicate a characteristic of the one or more associated ultrasound images.

According to examples in accordance with an aspect of the invention, there is provided an ultrasound imaging system comprising:

an ultrasound probe adapted to image a subject using an ultrasound imaging process to thereby generate one or more ultrasound images of the subject;

a probe manipulation sensor adapted to monitor a manipulation (e.g., a spatial manipulation) of the ultrasound probe during the ultrasound imaging process and generate a manipulation signal indicative of the manipulation (e.g., the spatial movement); and an ultrasound image processing system as described above.

BRIEF DESCRIPTION OF THE DRAWINGS

Examples of the invention will now be described in detail with reference to the accompanying drawings, in which.

DETAILED DESCRIPTION OF THE EMBODIMENTS

The invention provides a method for identifying a characteristic of one or more ultrasound images, wherein each image is of a subject imaged by an ultrasound probe using an ultrasound imaging process. The method includes obtaining a manipulation signal indicative of a manipulation of the ultrasound probe during the imaging process. A portion of the manipulation signal, which indicates the manipulation of the probe during a time period, is obtained. The obtained portion is associated with one or more ultrasound images. A neural network system is then used to classify a characteristic of the one or more ultrasound images based on both the obtained portion of the manipulation signal and the one or more images themselves. Such classification comprises applying one or more convolution kernels on the obtained portion of the manipulation signal to generate a convolution output representative of the obtained portion of the manipulation signal, and classifying the convolution output to indicate the characteristic of the one or more ultrasound images associated with the obtained portion.

Figure 1:
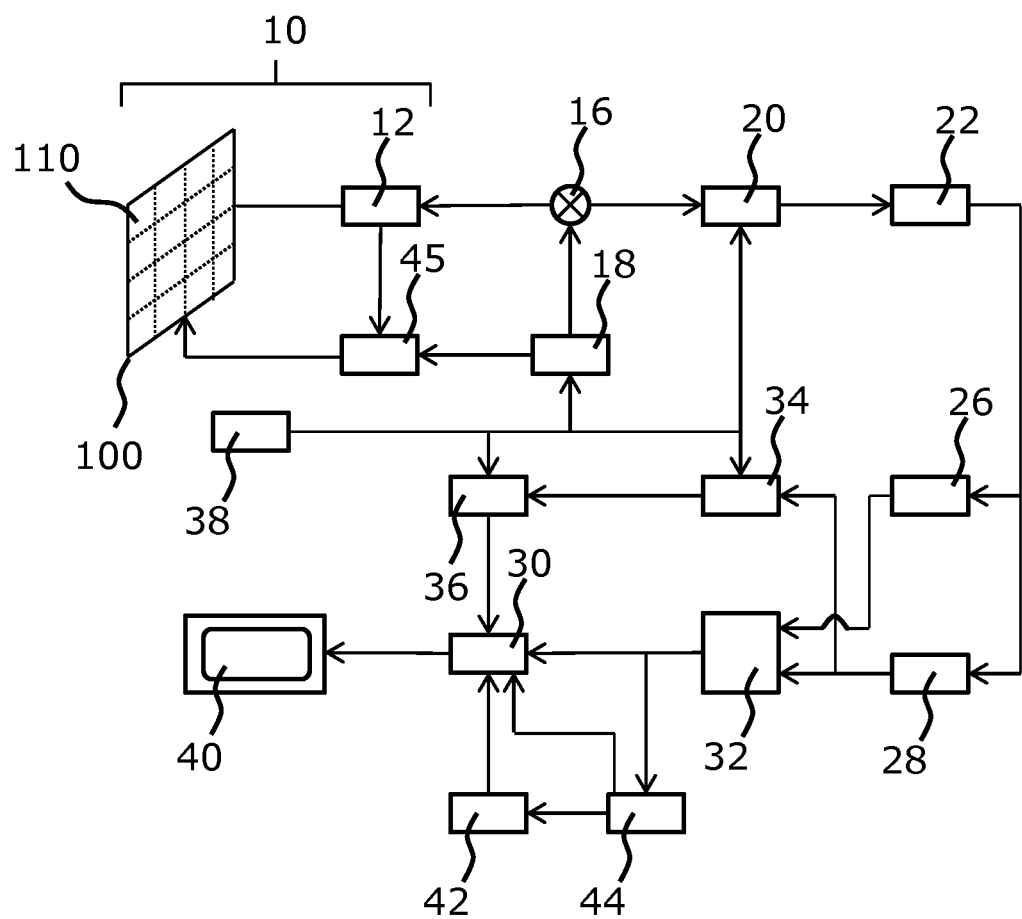
FIG. 1 shows an ultrasound diagnostic imaging system to explain the general operation.

The general operation of an exemplary ultrasound diagnostic imaging system will first be described, with reference to FIG. 1, and with emphasis on the signal processing function of the system since this invention relates to the processing of the signals measured by the transducer array.

The system comprises an array transducer probe 10 which has a CMUT transducer array 100 for transmitting ultrasound waves and receiving echo information. The transducer array 100 may alternatively comprise piezoelectric transducers formed of materials such as PZT or PVDF. The transducer array 100 is a two-dimensional array of transducers 110 capable of scanning in a 2D plane or in three dimensions for 3D imaging. In another example, the transducer array may be a 1D array.

The transducer array 100 is coupled to a microbeamformer 12 in the probe which controls reception of signals by the CMUT array cells or piezoelectric elements. Microbeamformers are capable of at least partial beamforming of the signals received by sub-arrays (or "groups" or "patches") of transducers as described in U.S. Pat. No. 5,997,479 (Savord et al.), U.S. Pat. No. 6,013,032 (Savord), and U.S. Pat. No. 6,623,432 (Powers et al.).

Note that the microbeamformer is entirely optional. The examples below assume no analog beamforming.

The microbeamformer 12 is coupled by the probe cable to a transmit/receive (T/R) switch 16 which switches between transmission and reception and protects the main beamformer 20 from high energy transmit signals when a microbeamformer is not used and the transducer array is operated directly by the main system beamformer. The transmission of ultrasound beams from the transducer array 10 is directed by a transducer controller 18 coupled to the microbeamformer by the T/R switch 16 and a main transmission beamformer (not shown), which receives input from the user's operation of the user interface or control panel 38.

One of the functions controlled by the transducer controller 18 is the direction in which beams are steered and focused. Beams may be steered straight ahead from (orthogonal to) the transducer array, or at different angles for a wider field of view. The transducer controller 18 can be coupled to control a DC bias control 45 for the CMUT array. The DC bias control 45 sets DC bias voltage(s) that are applied to the CMUT cells.

In the reception channel, partially beamformed signals are produced by the microbeamformer 12 and are coupled to a main receive beamformer 20 where the partially beamformed signals from individual patches of transducers are combined into a fully beamformed signal. For example, the main beamformer 20 may have 128 channels, each of which receives a partially beamformed signal from a patch of dozens or hundreds of CMUT transducer cells or piezoelectric elements. In this way the signals received by thousands of transducers of a transducer array can contribute efficiently to a single beamformed signal.

The beamformed reception signals are coupled to a signal processor 22. The signal processor 22 can process the received echo signals in various ways, such as band-pass filtering, decimation, I and Q component separation, and harmonic signal separation which acts to separate linear and nonlinear signals so as to enable the identification of nonlinear (higher harmonics of the fundamental frequency) echo signals returned from tissue and micro-bubbles. The signal processor may also perform additional signal enhancement such as speckle reduction, signal compounding, and noise elimination. The band-pass filter in the signal processor can be a tracking filter, with its pass band sliding from a higher frequency band to a lower frequency band as echo signals are received from increasing depths, thereby rejecting the noise at higher frequencies from greater depths where these frequencies are devoid of anatomical information.

The beamformers for transmission and for reception are implemented in different hardware and can have different functions. Of course, the receiver beamformer is designed to take into account the characteristics of the transmission beamformer. In FIG. 1 only the receiver beamformers 12, 20 are shown, for simplicity. In the complete system, there will also be a transmission chain with a transmission micro beamformer, and a main transmission beamformer.

The function of the micro beamformer 12 is to provide an initial combination of signals in order to decrease the number of analog signal paths. This is typically performed in the analog domain.

The final beamforming is done in the main beamformer 20 and is typically after digitization.

The transmission and reception channels use the same transducer array 10' which has a fixed frequency band. However, the bandwidth that the transmission pulses occupy can vary depending on the transmission beamforming that has been used. The reception channel can capture the whole transducer bandwidth (which is the classic approach) or by using bandpass processing it can extract only the bandwidth that contains the useful information (e.g. the harmonics of the main harmonic).

The processed signals are coupled to a B mode (i.e. brightness mode, or 2D imaging mode) processor 26 and a Doppler processor 28. The B mode processor 26 employs detection of an amplitude of the received ultrasound signal for the imaging of structures in the body such as the tissue of organs and vessels in the body. B mode images of structure of the body may be formed in either the harmonic image mode or the fundamental image mode or a combination of both as described in U.S. Pat. No. 6,283,919 (Roundhill et al.) and U.S. Pat. No. 6,458,083 (Jago et al.) The Doppler processor 28 processes temporally distinct signals from tissue movement and blood flow for the detection of the motion of substances such as the flow of blood cells in the image field. The Doppler processor 28 typically includes a wall filter with parameters which may be set to pass and/or reject echoes returned from selected types of materials in the body.

The structural and motion signals produced by the B mode and Doppler processors are coupled to a scan converter 32 and a multi-planar reformatter 44. The scan converter 32 arranges the echo signals in the spatial relationship from which they were received in a desired image format. For instance, the scan converter may arrange the echo signal into a two dimensional (2D) sector-shaped format, or a pyramidal three dimensional (3D) image. The scan converter can overlay a B mode structural image with colors corresponding to motion at points in the image field with their Doppler-estimated velocities to produce a color Doppler image which depicts the motion of tissue and blood flow in the image field. The multi-planar reformatter will convert echoes which are received from points in a common plane in a volumetric region of the body into an ultrasound image of that plane, as described in U.S. Pat. No. 6,443,896 (Detmer). A volume renderer 42 converts the echo signals of a 3D data set into a projected 3D image as viewed from a given reference point as described in U.S. Pat. No. 6,530,885 (Entrekin et al.).

The 2D or 3D images are coupled from the scan converter 32, multi-planar reformatter 44, and volume renderer 42 to an image processor 30 for further enhancement, buffering and temporary storage for display on an image display 40. In addition to being used for imaging, the blood flow values produced by the Doppler processor 28 and tissue structure information produced by the B mode processor 26 are coupled to a quantification processor 34. The quantification processor produces measures of different flow conditions such as the volume rate of blood flow as well as structural measurements such as the sizes of organs and gestational age. The quantification processor may receive input from the user control panel 38, such as the point in the anatomy of an image where a measurement is to be made. Output data from the quantification processor is coupled to a graphics processor 36 for the reproduction of measurement graphics and values with the image on the display 40, and for audio output from the display device 40. The graphics processor 36 can also generate graphic overlays for display with the ultrasound images. These graphic overlays can contain standard identifying information such as patient name, date and time of the image, imaging parameters, and the like. For these purposes the graphics processor receives input from the user interface 38, such as patient name. The user interface is also coupled to the transmit controller 18 to control the generation of ultrasound signals from the transducer array 10' and hence the images produced by the transducer array and the ultrasound system. The transmit control function of the controller 18 is only one of the functions performed. The controller 18 also takes account of the mode of operation (given by the user) and the corresponding required transmitter configuration and band-pass configuration in the receiver analog to digital converter. The controller 18 can be a state machine with fixed states.

The user interface is also coupled to the multi-planar reformatter 44 for selection and control of the planes of multiple multi-planar reformatted (MPR) images which may be used to perform quantified measures in the image field of the MPR images.

The controller 18 may be further adapted to perform any part of the methods described below with reference to FIGS. 2 to 4. Alternatively, these methods may be performed by a separate controller, or a plurality of controllers.

Figure 2:
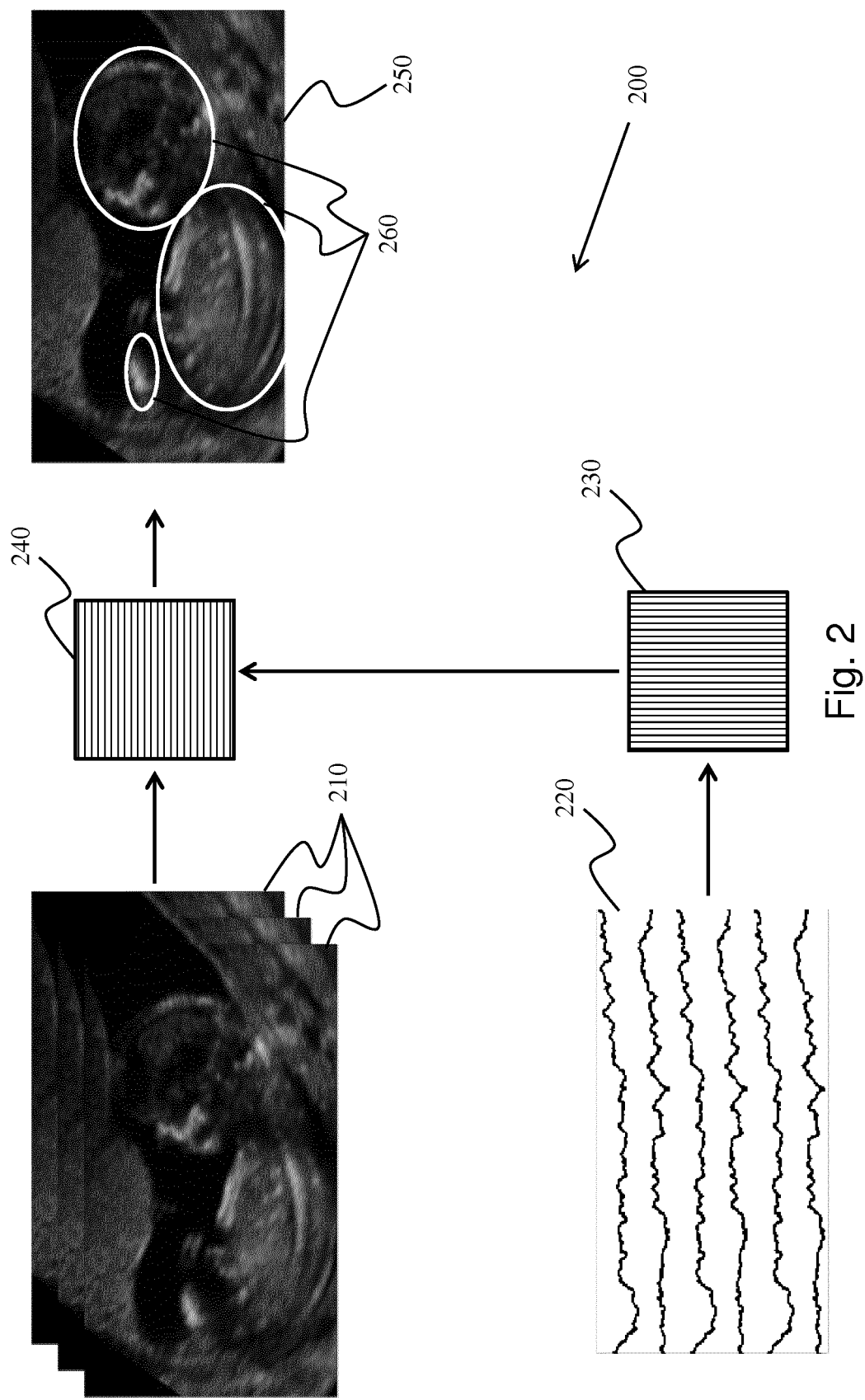
FIG. 2 shows a method of the invention.

FIG. 2 shows a general method 200 of the invention. In a first step, an ultrasound probe 10 (shown in FIG. 1) acquires one or more ultrasound images 210 as a first input. In addition to the ultrasound images, the movements of the probe whilst recording the one or more ultrasound images are recorded in the form of a manipulation signal 220.

The manipulation signal 220 may be a collection of signals captured by a plurality of sensors located within the probe, such as: accelerometers, gyroscopes and magnetometers. The manipulation signal is provided to a combined convolution neural network—long short-term memory (CNN-LSTM) processing stage 230, the operation of which is described below with reference to FIG. 3. The output of this processing stage is a summary of probe manipulation patterns that span the time associated with the acquisition of the one or more ultrasound images 210, which is fed into a further neural network 240.

This further neural network 240, which may for example be a deep convolutional network such as a U-Net architecture, receives both the manipulation patterns from the CNN-LSTM processing stage 230 and the one or more ultrasound image 210. Using both the manipulation patterns of the ultrasound probe and the associated ultrasound images, the further neural network performs image segmentation on the ultrasound images to produce a segmented ultrasound image 250 having one or more classified features 260. The neural networks of this system, 230 and 240, may comprise both convolutional and recurrent neural networks adapted to combine the image and manipulation signal data modalities.

In other words, in addition to ultrasound image signals, ultrasound probe manipulation and/or orientation signals are used for image segmentation and/or image feature classification. The neural network architectures typically employed for image segmentation, such as U-Net and encoder-decoder networks, are additionally conditioned using the probe manipulation sensor signals. The system may be adapted to produce the segmented image 250 output at a desired frame rate depending on the application of the ultrasound system. In addition to producing a segmented ultrasound image, the further neural network 240 may also be adapted to generate biometric measurements based on the one or more ultrasound images and probe manipulation signals.

Figure 3:
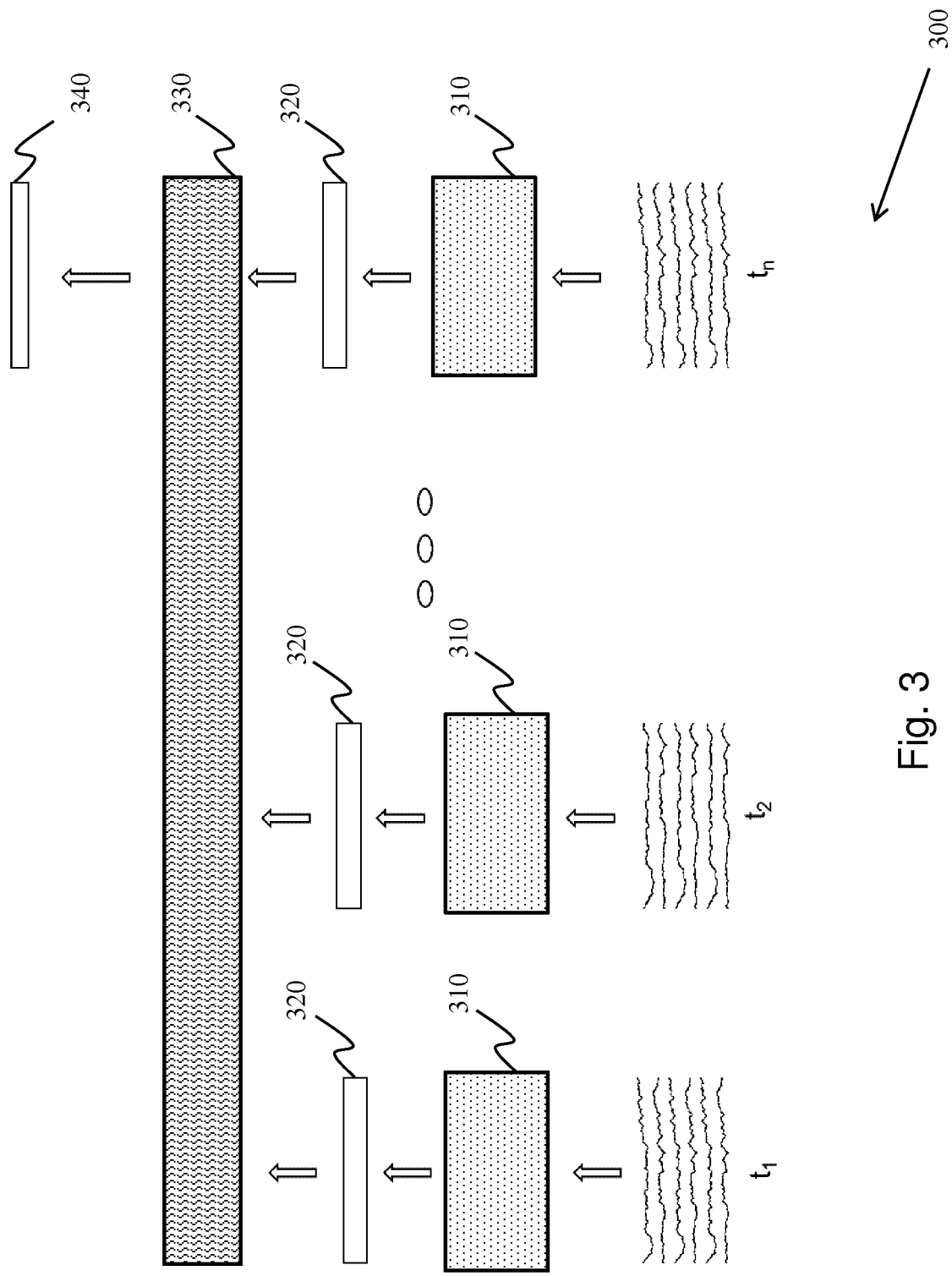
FIG. 3 shows a method of the convolution neural network—long short-term memory used in the method shown in FIG. 2.

FIG. 3 shows an exemplary CNN-LSTM architecture 300 for processing the probe manipulation signals.

The orientation and manipulation of the ultrasonic probe during image acquisition influences the quality and interpretation of ultrasound images. For example, the ultrasound probe may be rotated without the monitor position changing, which may create confusion in the interpretation of the orientation of an organ or a fetus. Sonographers typically use an orientation marker on the probe and compare it to a marker on a display 40 of the ultrasound system to determine the correct orientation of the image. For automatic segmentation of the ultrasound images, the ultrasound system also needs to determine the orientation of the ultrasound image so that it can more easily identify which features, such as organs, are expected in a given position on the screen.

As such, probe manipulation is an important consideration in producing high quality ultrasound images. There are several known definitions of probe manipulations, such as: slide; rock; sweep; fan; pressure/compression; rotation; tilt; and alignment. It is possible to train the CNN-LSTM network to identify these motions and correlate their combinations with certain features, such as organs of a fetus, in certain probe orientations.

FIG. 3 shows a collection of probe manipulation signals ($t_1, t_2, \ldots, t_N$), each representing the manipulation of the probe during a given time window. The probe manipulation signal within the time window is referred to as a portion of the probe manipulation signal. The length of the time window, and so the size of the signal portion, varies depending on the required frame rate of the ultrasound system.

Each of the manipulation signal portions are processed by one-dimensional convolutional kernels 310 by way of the CNN. The convolutional kernels capture local temporal patterns 320 within the probe manipulation signal portions. However, these local temporal patterns may not be sufficient to represent the complete manipulation of the probe during the acquisition of an ultrasound image. Thus, a long-term temporal pattern may be required to fully describe the motion of the ultrasound probe.

The local temporal patterns 320 may then be supplied to an LSTM 330, which builds up a long-term temporal pattern of the probe manipulation signal portions. In this way, the LSTM may detect patterns in the probe manipulation signals with time spans longer than that of the manipulation signal portions. Together, the CNN and LSTM capture both short-term and long-term patterns that accurately represent a sonographer's probe manipulation operations. The output 340 of the LSTM is reshaped and fed as a feature map to the U-Net architecture 240 to be used in the segmentation of the one or more ultrasound images 210.

By way of example, there may be 9 sensor signals including: 3 accelerometer signals; 3 gyroscope signals; and 3 magnetometer signals. In this case, the 9 probe signals constitute time series data from nine channels. In matrix form, the time series data has the format C×N, where C is the number of input channels and N is the length of the time series data, i.e. the total number of samples. To prepare the time series data for pattern recognition by way of the CNN and LSTM, the time series data is split into a sequence of overlapping manipulation signal portions, each of length M, wherein the overlap size can be up to M/2. Each manipulation signal portion of shape C×M is processed with one-dimensional convolutional and pooling, also referred to as downsampling, layers.

Taking this example further, the ultrasound probe manipulation sensors, such as an accelerometer, a gyroscope and/or a magnetometer, may provide a manipulation signal at a rate of 60 samples per second. Taking 1 second to be the size of the manipulation signal portions, the one-dimensional convolutional and pooling layers are applied to these 1 second segments. It should be noted that the segments overlap each other by 30 samples, or half a second. Tables 1 and 2 below show details of an example network architecture for processing these 1-second segments using the CNN and LSTM, respectively.

TABLE 1

CNN model comprising three one-dimensional convolution layers (Conv1, Conv2 and Conv3) and three pooling layers (Pool1, Pool2 and Pool3)

| Layer | Conv1 | Pool1 | Conv2 | Pool2 | Conv3 | Pool3 |
| --- | --- | --- | --- | --- | --- | --- |
| Size | 5 | 2 | 3 | 2 | 3 | 4 |
| Stride | 2 | 2 | 1 | 2 | 1 | 4 |
| Filters | 64 | — | 128 | — | 256 | — |
| Input shape | 60 × 9 | 28 × 64 | 14 × 64 | 12 × 128 | 6 × 256 | 4 × 256 |
| Output shape | 28 × 64 | 14 × 64 | 12 × 64 | 6 × 128 | 4 × 256 | 256 |

This model processes manipulation signal portions of one second, which take the form of a 60×9 data matrix. In a convolutional layer, for example Conv1, the filter acts to perform element wise multiplications between the values in the filter matrix, referred to as weights, and the values of the input data. The size of the filter controls which values of the input data are subject to this element wise multiplication. In the case of Conv 1, the filter is one-dimensional and has a length of 5. The results of the various multiplications are then summed and passed through element-wise non-linear functions such as rectified linear units (ReLUs) and sigmoids (these are known as activation functions) to produce a first data point of the output matrix. The filter then moves by a given amount, referred to as the stride, across the input data matrix and repeats the element wise multiplication, thereby generating the second data point of the output matrix. This process is repeated until the filter has processed each possible position in the input data matrix.

This example thus results in 28 data points in the output matrix for each row of the input matrix.

By way of example, the manipulation sensors may produce 60 samples per second, and each sample has 9 numbers. In a portion of 1 second, a 60×9 data matrix results, and this data is run through Conv1 with 64 filters to create data of shape 28×64. This data is then fed to the subsequent layer of the network.

Because time could be running for a very long time and it is not possible to efficiently process data with a long temporal extent, only portions of the samples are analyzed. In this case, 1 second samples are used for identifying local patterns and for patterns with long-term dependencies, a longer time period is used such as 10 seconds. The decision making frequency may also be selected according to the application. For example, a decision may be taken every second using the last 10 seconds of data.

The pooling layers act to downsample the output of the convolution layers, thereby reducing the processing power required to operate the CNN. In addition, the pooling layers serve to reduce the problem of overfitting when training the neural network.

The final output of this CNN model is a 256 point one-dimensional vector for each manipulation signal portion. A sequence of several of these 256-vectors form the local temporal patterns 320 that are fed to the LSTM 330.

TABLE 2

LSTM network model comprising two LSTM layers and one dense layer

| Layer | LSTM | LSTM | Fully connected |
|---|---|---|---|
| Filters | 64 | 64 | 65536 = (256*256) |
| Input shape | (any, 256) | (any, 64) | 64 |
| Output shape | (any, 64) | 64 | (256, 256, 1) |

LSTMs are a type of recurrent neural network that are capable of learning long-term dependencies and recognizing long-term patterns. The general way the recurrent neural network functions is outlined below with reference to the one particular example described above.

In this example, a sequence of 256 vectors can together form patterns with long-term dependencies. For probe manipulation, the long-term patterns can span 10 seconds. For a 10 second probe manipulation, there will be 20 segments (with the assumption of 1 second long segments and half-a-second overlaps). This means that the input to the LSTM subnetwork is a 20×256 matrix (representing 10 seconds of probe manipulation).

The LSTM subnetwork then takes the 20×256 data matrix as input. It has two LSTM layers, each having 64 filters. The first LSTM layer takes the 20×256 matrix and processes each segment vector and produces an output vector of size 64. The processing is implemented sequentially, segment by segment.

When processing each segment vector, the LSTM also makes use of a copy of its output from the previous segment vector (of course, for the first segment, starting conditions need to be defined, such as the previous output being set to zeros). The output at the previous segment functions as a memory of the LSTM and is used when it produces an output for the current input.

At the end of the sequence, the output of the first LSTM layer is a 20×64 data matrix. The 20×64 output is now an input to the second LSTM layer, which performs the same function as the first LSTM layer apart from two differences: (i) the input is now the 20×64 data matrix instead of the 20×256 data matrix; and (ii) the output of only the last segment is kept, because the last output vector is a combined result of all segments in the sequence (achieved recursively).

After the second and final LSTM layer, there is a dense layer whose connection weights ensure that the 64-vector output of the final LSTM can be reshaped to look like an image signal (in this example 256×256×1). This output has the shape of a feature map and is fed into the last convolution layer of the U-Net architecture as shown in FIG. 4 (described below).

The last convolution layer is where decisions are made and by putting the processed probe information in the last convolution layer, the probe information is able to influence the decision-making processing of the network as directly as possible.

Figure 4:
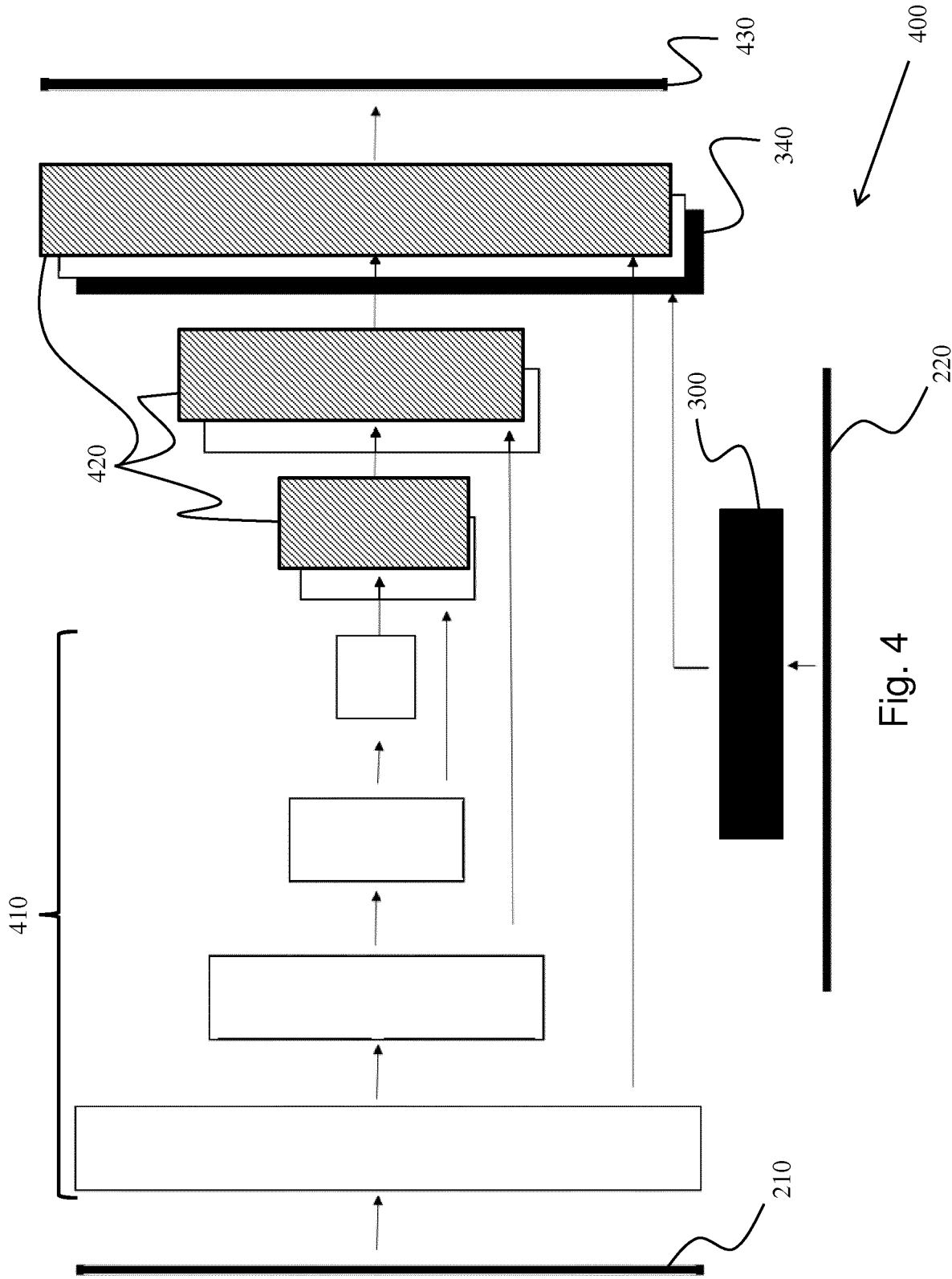
FIG. 4 shows a method of the further neural network used in the method shown in FIG. 2.

FIG. 4 shows an extended U-Net architecture 400 for processing both the one or more ultrasound images 210 and the output of the CNN-LSTM architecture 300. Standard U-Net architectures, which are known in the field of medical image segmentation, typically take in an image and produce a segmented output image of the same resolution.

The U-Net architecture is a form of convolutional neural network and functions in a largely similar manner to the CNN model described above in the first part of the operation 410. This first part involves passing the one or more ultrasound images through a series of convolution and pooling layers, wherein the input data matrix comprises the pixel values of the images.

The U-Net architecture further comprises a series of upsampling layers 420, where earlier layer outputs (shown as white boxes) are concatenated with the upsampled layers before being passed to subsequent layers. After the last upsampling layer and before the last convolution layers, the output from the CNN-LSTM 340 is reshaped as a feature map and depthwise concatenated with the feature maps of the final upsampling layer. An example of the details of a U-Net architecture are shown in Table 3 below using an example input image of shape (256,256,1), where conv2d_N represents the $N^{th}$ convolution layer and average_pooling2d_N represents the $N^{th}$ pooling layer. In addition, concatenate_N represents the $N^{th}$ concatenation layer which combines the earlier layer outputs with the upsampled layers. The last input layer of the U-Net is combined with the CNN-LSTM output before performing the image segmentation or classification. Alternatively, the CNN-LSTM output may be introduced to the U-Net network earlier in the workflow. In principle, it also possible to put another CNN-LSTM layer whose outputs are connected to early stages of the U-Net architecture.

TABLE 3

U-Net neural network architecture for an input image of shape (256, 256, 1)

| Layers | Filter size | Filters | # Strides | Input shape | Output shape |
|---|---|---|---|---|---|
| conv2d_1 | (3, 3) | (1, 1) | 32 | (256, 256, 1) | (256, 256, 32) |
| conv2d_2 | (3, 3) | (1, 1) | 32 | (256, 256, 32) | (256, 256, 32) |
| average_pooling2d_1 | — | (2, 2) | — | (256, 256, 32) | (128, 128, 32) |
| conv2d_3 | (3, 3) | (1, 1) | 64 | (128, 128, 32) | (128, 128, 64) |
| conv2d_4 | (3, 3) | (1, 1) | 64 | (128, 128, 64) | (128, 128, 64) |
| average_pooling2d_2 | — | (2, 2) | — | (128, 128, 64) | (64, 64, 64) |
| conv2d_5 | (3, 3) | (1, 1) | 128 | (64, 64, 64) | (64, 64, 128) |
| conv2d_6 | (3, 3) | (1, 1) | 128 | (64, 64, 128) | (64, 64, 128) |
| average_pooling2d_3 | — | (2, 2) | — | (64, 64, 128) | (32, 32, 128) |
| conv2d_7 | (3, 3) | (1, 1) | 256 | (32, 32, 128) | (32, 32, 256) |
| conv2d_8 | (3, 3) | (1, 1) | 256 | (32, 32, 256) | (32, 32, 256) |
| average_pooling2d_4 | — | (2, 2) | — | (32, 32, 256) | (16, 16, 256) |
| conv2d_9 | (3, 3) | (1, 1) | 512 | (16, 16, 256) | (16, 16, 512) |
| conv2d_10 | (3, 3) | (1, 1) | 512 | (16, 16, 512) | (16, 16, 512) |
| conv2d_transpose_1 | (2, 2) | (2, 2) | 256 | (16, 16, 512) | (32, 32, 256) |
| concatenate_1 | — | — | — | [(32, 32, 256), (32, 32, 256)] | (32, 32, 512) |
| conv2d_11 | (3, 3) | (1, 1) | 256 | (32, 32, 512) | (32, 32, 256) |
| conv2d_12 | (3, 3) | (1, 1) | 256 | (32, 32, 256) | (32, 32, 256) |
| conv2d_transpose_2 | (2, 2) | (2, 2) | 128 | (32, 32, 256) | (64, 64, 128) |
| concatenate_2 | — | — | — | [(64, 64, 128), (64, 64, 128)] | (64, 64, 256) |
| conv2d_13 | (3, 3) | (1, 1) | 128 | (64, 64, 256) | (64, 64, 128) |
| conv2d_14 | (3, 3) | (1, 1) | 128 | (64, 64, 128) | (64, 64, 128) |
| conv2d_transpose_3 | (2, 2) | (2, 2) | 64 | (64, 64, 128) | (128, 128, 64) |
| concatenate_3 | — | — | — | [(128, 128, 64), (128, 128, 64)] | (128, 128, 128) |
| conv2d_15 | (3, 3) | (1, 1) | 64 | (128, 128, 128) | (128, 128, 64) |
| conv2d_16 | (3, 3) | (1, 1) | 64 | (128, 128, 64) | (128, 128, 64) |
| conv2d_transpose_4 | (2, 2) | (2, 2) | 32 | (128, 128, 64) | (256, 256, 32) |
| concatenate_4 | — | — | — | [(256, 256, 32), (256, 256, 32)] | (256, 256, 64) |
| conv2d_17 | (3, 3) | (1, 1) | 32 | (256, 256, 64) | (256, 256, 32) |
| conv2d_18 | (3, 3) | (1, 1) | 32 | (256, 256, 32) | (256, 256, 32) |
| conv2d_19 | (1, 1) | (1, 1) | 1 | (256, 256, 32) | (256, 256, any) |

Thus, the fusing of the information coming from the probe manipulation and from the US images can be combined in various ways: at the last layer as in the example above or at an earlier layer. Fusing may take place at both early and late layers, using respective sub-networks specializing in early and late fusions.

The architecture presented in Table 3 is of course just an example presented for completeness, and it is not intended to be limiting.

The system may then perform one of three functions based on the output of the final layer 430 of the U-Net architecture 400. These functions are: standard view detection; image segmentation; and biometric measurements.

In the case of standard view detection, the system may be used to automatically detect commonly acquired standard image views in clinical ultrasound images. For example, a fetal abnormality screening program in the UK requires 12 standard views to be saved. The system may naturally detect standard scan planes based on the one or more ultrasound images and the probe manipulation signal. The standard views typically correspond to image views where the probe is held still for a period of time after it has been correctly positioned by the sonographer using a pre-defined protocol of probe manipulation. The sonographer's probe manipulation signals provide valuable information about which images are standard or good views.

In the case of image segmentation, out of the detected standard or required ultrasound views, segmentation of anatomical structures of the subject can be made. For example, when the ultrasound system is being used to scan a fetus, the head, hands, abdomen, legs and other similar organ structures can be identified and marked as such. The segmentation may be used to enhance the image and colorize the fetus to give it a more easily identifiable appearance. The segmentation may further be employed for automated breast cancer detection and classification or ultrasound nerve segmentation.

In the case of biometric measurements, biometric measurements may be made automatically using the segmentation output of the system and may then be used to detect anomalies and monitor, for example, fetal growth. It is also possible to train the neural network to produce these measurements from the system together with the segmentation output. The joint training of the network architecture for segmentation and regression (biometric measurements) forces the network to produce segmentations and regressions that support each other.

The system may be trained from a set of ultrasound images pre-annotated with anatomical structures (and if available, also the biometric measurements).

Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A computer-implemented method of identifying a characteristic of one or more ultrasound images, wherein each ultrasound image is of a subject imaged by an ultrasound probe using an ultrasound imaging process, the method comprising:

obtaining a manipulation signal indicative of a manipulation of the ultrasound probe during the ultrasound imaging process;

obtaining a portion of the manipulation signal ($t_n$), the obtained portion indicating the manipulation of the ultrasound probe during a time period, wherein the obtained portion is associated with one or more ultrasound images; and classifying, using a neural network system, a characteristic of the one or more associated ultrasound images based on both the one or more ultrasound images and the obtained portion of the manipulation signal, wherein classifying the characteristic of the one or more associated ultrasound images comprises applying one or more convolution kernels on the obtained portion of the manipulation signal to generate a convolution output representative of the obtained portion of the manipulation signal, and classifying the convolution output to indicate the characteristic of the one or more ultrasound images associated with the obtained portion.

2. The computer-implemented method of claim 1, wherein the step of classifying the characteristic of the one or more associated ultrasound images comprises:

a) classifying whether the obtained portion of the manipulation signal is associated with one of:
   a high quality ultrasound image;
   an ultrasound image of a predetermined view of the subject; and
   a presence of one or more predetermined regions of interest of the subject in the associated one or more ultrasound images; and b) identifying the characteristic of the one or more associated ultrasound images by means of assigning the classification of the obtained portion as the characteristic of the one or more associated ultrasound images.

3. The computer-implemented method of claim 1, wherein the step of classifying the characteristic of the one or more associated ultrasound images comprises:

segmenting the manipulation signal into a plurality of portions, each portion being associated with a same one or more ultrasound images;

applying one or more convolutional kernels to each obtained portion of the manipulation signal to generate a convoluted output of each time segment; and processing the convoluted output of each time segment using a long short-term memory to classify each obtained portion.

4. The computer-implemented method of claim 1, wherein:

the step of obtaining a manipulation signal comprises obtaining a plurality of manipulation signals, each indicative of a manipulation of the ultrasound probe during the ultrasound imaging process;

the step of obtaining a portion of the manipulation signal comprises obtaining a plurality of temporally associated portions by obtaining a temporally associated portion from each manipulation signal, wherein the plurality of temporally associated portions are associated with a same one or more ultrasound images; and the step of classifying the characteristic of the one or more associated ultrasound images comprises classifying the plurality of temporally associated portions to indicate a characteristic of the one or more associated ultrasound images.

5. The computer-implemented method of claim 4, wherein classifying the plurality of temporally associated portions comprises:

obtaining a two-dimensional data structure representative of the plurality of temporally associated portions;

applying a convolutional kernel to the two-dimensional data structure to generate a convolution output of the two-dimensional data structure; and classifying the convolutional output to indicate a characteristic of the one or more associated ultrasound images.

6. The computer-implemented method of claim 5, wherein:

the step of obtaining a portion of the manipulation signal comprises obtaining two or more pluralities of temporally associated portions of the manipulation signals, wherein each of the pluralities are associated with a same one or more ultrasound images; and the step of classifying the characteristic of the one or more associated ultrasound images comprises:

a) obtaining a plurality of two-dimensional data structures, each data structure being representative of a different plurality of temporally associated portions;

b) applying a convolutional kernel to each two-dimensional data structure to generate a respective plurality of convolution outputs; and c) processing the plurality of convolution outputs using a long short-term memory to classify the two or more pluralities of temporally associated portions and thereby indicate a characteristic of the one or more associated ultrasound images.

7. The computer-implemented method of claim 1, wherein the manipulation signal is indicative of one or more of:

a location of the ultrasound probe with respect to the subject; an angle of the ultrasound probe with respect to the subject;

an orientation of the ultrasound probe with respect to the subject; a pressure applied by the ultrasound probe on the subject;

an acceleration of the ultrasound probe with respect to the subject; a direction of movement of the ultrasound probe; and a pattern of movement of the ultrasound probe.

8. The computer-implemented method of claim 1, further comprising segmenting the ultrasound image.

9. The computer-implemented method of claim 8, further comprising overlaying, on each selected ultrasound image, a respective segmented region of interest.

10. A non-transitory computer-readable medium, comprising code means for implementing the computer-implemented method of claim 1 when said program is run on a computer.

11. An ultrasound image processing system adapted to identify a characteristic of one or more ultrasound images, wherein the ultrasound image is of a subject imaged by an ultrasound probe using an ultrasound imaging process, the ultrasound image processing system being adapted to:

obtain a manipulation signal indicative of a manipulation of the ultrasound probe during the ultrasound imaging process;

obtain a portion of the manipulation signal ($t_n$), the obtained portion indicating a manipulation of the ultrasound probe during a time period, wherein the obtained portion is associated with one or more ultrasound images; and classify, using a neural network system, a characteristic of the one or more associated ultrasound images based on both the one or more ultrasound images and the obtained portion of the manipulation signal, wherein the ultrasound image processing system is adapted to classify the characteristic of the one or more associated ultrasound images by applying one or more convolution kernels on the obtained portion of the manipulation signal to generate a convolution output representative of the obtained portion of the manipulation signal, and classifying the convolution output to indicate the characteristic of the one or more ultrasound images associated with the obtained portion.

12. The ultrasound image processing system of claim 11, wherein the ultrasound image processing system is adapted to classify the characteristic of the one or more associated ultrasound images by:

segmenting the manipulation signal into a plurality of portions, each portion being associated with a same one or more ultrasound images;

applying one or more convolutional kernels to each obtained portion of the manipulation signal to generate a convoluted output of each time segment; and processing the convoluted output of each time segment using a long short-term memory to classify each obtained portion.

13. The ultrasound image processing system of claim 11, wherein the ultrasound image processing system is further adapted to:

obtain a plurality of manipulation signals, each indicative of a manipulation of the ultrasound probe during the ultrasound imaging process;

obtain a plurality of temporally associated portions by obtaining a temporally associated portion from each manipulation signal, wherein the plurality of temporally associated portions are associated with a same one or more ultrasound images; and classify the plurality of temporally associated portions to indicate a characteristic of the one or more associated ultrasound images.

14. The ultrasound image processing system of claim 13, wherein the ultrasound image processing system is adapted to classify the plurality of temporally associated portions by:

obtaining a two-dimensional data structure representative of the plurality of temporally associated portions;

applying a convolutional kernel to the two-dimensional data structure to generate a convolution output of the two-dimensional data structure; and classifying the convolutional output to indicate a characteristic of the one or more associated ultrasound images.

15. An ultrasound imaging system comprising:

an ultrasound probe adapted to image a subject using an ultrasound imaging process to thereby generate one or more ultrasound images of the subject;

a probe manipulation sensor adapted to monitor a manipulation of the ultrasound probe during the ultrasound imaging process and generate a manipulation signal indicative of the manipulation; and an ultrasound image processing system of claim 11.

* * * * *